United States Patent
Reichwein

(10) Patent No.: US 7,754,892 B2
(45) Date of Patent: Jul. 13, 2010

(54) PROCESSES FOR THE PREPARATION OF N-(2-ACETYL-4,6-DIMETHYLPHENYL)-3-{[(3,4 DIMETHYL-5-ISOXAZOLYL)AMINO]SULFONYL}-2-THIOPHENECARBOXAMIDE

(75) Inventor: John F. Reichwein, Houston, TX (US)

(73) Assignee: Encysive Pharmaceuticals, Inc., New York, NY (US)

( * ) Notice: Subject to any disclaimer, the term of this patent is extended or adjusted under 35 U.S.C. 154(b) by 434 days.

(21) Appl. No.: 11/890,201

(22) Filed: Aug. 3, 2007

(65) Prior Publication Data

US 2008/0086011 A1    Apr. 10, 2008

Related U.S. Application Data

(60) Provisional application No. 60/835,636, filed on Aug. 4, 2006.

(51) Int. Cl.
*C07D 413/12* (2006.01)
*C07D 333/38* (2006.01)
(52) U.S. Cl. .......................................... 548/246; 549/64
(58) Field of Classification Search ....................... None
See application file for complete search history.

(56) References Cited

U.S. PATENT DOCUMENTS 6,686,382 B2    2/2004    Wu et al. ..................... 514/380

*Primary Examiner*—Kamal A Saeed
(74) *Attorney, Agent, or Firm*—Gregg C. Benson; Robert T. Ronau

(57) ABSTRACT

Provided are processes for the preparation of N-(2-acetyl-4,6-dimethylphenyl)-3-{[(3,4 dimethyl-5-isoxazolyl)amino]sulfonyl}-2-thiophenecarboxamide, a compound useful for the treatment of endothelin-mediated disorders.

48 Claims, No Drawings

PROCESSES FOR THE PREPARATION OF N-(2-ACETYL-4,6-DIMETHYLPHENYL)-3-{[(3,4 DIMETHYL-5-ISOXAZOLYL)AMINO] SULFONYL}-2-THIOPHENECARBOXAMIDE

1. RELATED APPLICATION

Priority is claimed herein to under 35 U.S.C. §119(e) to U.S. Provisional Patent Application No. 60/835,636, filed Aug. 4, 2006, entitled "PROCESSES FOR THE PREPARATION OF N-(2-ACETYL-4,6-DIMETHYLPHENYL)-3-{[(3,4 DIMETHYL-5-ISOXAZOLYL)AMINO]SULFONYL}-2-THIOPHENECARBOXAMIDE." The disclosure of the above-referenced application is incorporated herein by reference in its entirety.

2. FIELD

Provided herein are processes for the preparation of N-(2-acetyl-4,6-dimethylphenyl)-3-{[(3,4 dimethyl-5-isoxazolyl) amino]sulfonyl}-2-thiophenecarboxamide, a compound useful for the treatment of endothelin-mediated disorders.

3. BACKGROUND

N-(2-acetyl-4,6-dimethylphenyl)-3-{[(3,4 dimethyl-5-isoxazolyl)amino]sulfonyl}-2-thiophenecarboxamide is an endothelin antagonist (U.S. Pat. No. 6,686,382). Endothelin antagonists are useful for the treatment of hypertension such as peripheral circulatory failure, heart disease such as angina pectoris, cardiomyopathy, arteriosclerosis, myocardial infarction, pulmonary hypertension, vasospasm, vascular restenosis, Raynaud's disease, cerebral stroke such as cerebral arterial spasm, cerebral ischemia, late phase cerebral spasm after subarachnoid hemorrhage, asthma, bronchoconstriction, renal failure, particularly post-ischemic renal failure, cyclosporine nephrotoxicity such as acute renal failure, colitis, as well as other inflammatory diseases, endotoxic shock caused by or associated with endothelin, and other diseases in which endothelin has been implicated. Provided herein are processes for the preparation of N-(2-acetyl-4,6-dimethylphenyl)-3-{[(3,4 dimethyl-5-isoxazolyl)amino]sulfonyl}-2-thiophenecarboxamide.

4. SUMMARY

Provided herein are processes for the preparation of N-(2-acetyl-4,6-dimethylphenyl)-3-{[(3,4 dimethyl-5-isoxazolyl) amino]sulfonyl}-2-thiophenecarboxamide:

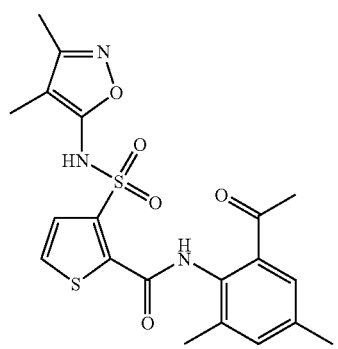

(I)

or a pharmaceutically acceptable derivative thereof.

In one aspect, provided is a process for preparing the compound of Formula (I), or a pharmaceutically acceptable derivative thereof, wherein the process involves a step of reacting a compound of Formula (II):

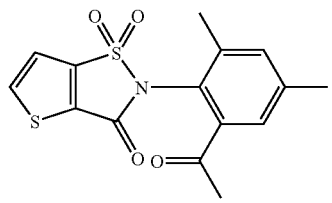

(II)

with a compound of Formula (III):

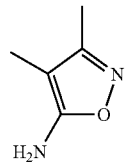

(III)

or a salt thereof.

5. DETAILED DESCRIPTION

5.1 Definitions

Unless defined otherwise, all technical and scientific terms used herein have the same meaning as is commonly understood by one of ordinary skill in the art to which this invention belongs. All patents, applications, published applications and other publications are incorporated by reference in their entirety. In the event that there are a plurality of definitions for a term herein, those in this section prevail unless stated otherwise.

As used herein, pharmaceutically acceptable derivatives of a compound include salts, esters, enol ethers, enol esters, acetals, ketals, orthoesters, hemiacetals, hemiketals, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris (hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, alk(en)(yn)yl, aryl, aralkyl, and cycloalkyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, alk(en)(yn)yl, aryl, aralkyl, or cycloalkyl. Pharmaceutically acceptable enol esters include, but are not limited to, derivatives of formula C=C(OC(O)R) where R is hydrogen, alkyl, alkenyl, alkynyl, aryl, aralkyl, or cycloalkyl. Pharmaceutically acceptable solvates and hydrates are complexes of a compound with one or more solvent or water molecules, or 1 to about 100, or 1 to about 10, or one to about 2, 3 or 4, solvent or water molecules.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

As used herein, alkyl refers to an unbranched or branched hydrocarbon chain. An alkyl group may be unsubstituted or substituted with one or more heteroatoms.

As used herein, alkenyl refers to an unbranched or branched hydrocarbon chain comprising one or more double bonds. The double bond of an alkenyl group may be unconjugated or conjugated to another unsaturated group. An alkenyl group may be unsubstituted or substituted with one or more heteroatoms.

As used herein, alkynyl refers to an unbranched or branched hydrocarbon chain comprising one of more triple bonds therein. The triple bond of an alkynyl group may be unconjugated or conjugated to another unsaturated group. An alkynyl group may be unsubstituted or substituted with one or more heteroatoms.

As used herein, alk(en)(yn)yl refers to an unbranched or branched hydrocarbon group comprising at least one double bond and at least one triple bond. The double bond or triple bond of an alk(en)(yn)yl group may be unconjugated or conjugated to another unsaturated group. An alk(en)(yn)yl group may be unsubstituted or substituted with one or more heteroatoms.

Exemplary alkyl, alkenyl, alkynyl, and alk(en)(yn)yl groups herein include, but are not limited to, methyl, ethyl, propyl, isopropyl, isobutyl, n-butyl, sec-butyl, tert-butyl, isopentyl, neopentyl, tert-pentyl, isohexyl, allyl (propenyl) and propargyl (propynyl).

As used herein, "aryl" refers to aromatic monocyclic or multicyclic groups containing from 6 to 19 carbon atoms. Aryl groups include, but are not limited to groups such as unsubstituted or substituted fluorenyl, unsubstituted or substituted phenyl, and unsubstituted or substituted naphthyl.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl or isoquinolinyl.

As used herein, "halo," "halogen," or "halide" refers to F, Cl, Br or I.

As used herein, base refers to any compound that accepts protons in water or solvent. Thus, exemplary bases include, but are not limited to, alkali metal hydroxides and alkali metal alkoxides (i.e., MOR, wherein M is an alkali metal such as but not limited to potassium, lithium, or sodium and R is hydrogen, alkyl, alkenyl, alkynyl, or alk(en)(yn)yl) such as but not limited to potassium hydroxide, potassium tert-butoxide, potassium tert-pentoxide, sodium hydroxide, sodium tert-butoxide, lithium hydroxide, etc.); other hydroxides such as but not limited to magnesium hydroxide (Mg(OH)$_2$), calcium hydroxide (Ca(OH)$_2$), or barium hydroxide (Ba(OH)$_2$); alkali metal hydrides (i.e., MH, wherein M is as defined above) such as but not limited to sodium hydride, potassium hydride, or lithium hydride; carbonates such as but not limited to potassium carbonate (K$_2$CO$_3$), sodium carbonate (Na$_2$CO$_3$), potassium bicarbonate (KHCO$_3$), or sodium bicarbonate (NaHCO$_3$); alkyl ammonium hydroxides, alkenyl ammonium hydroxides, alkynyl ammonium hydroxides, or alk(en)(yn)yl ammonium hydroxides such as but not limited to n-tetrabutyl ammonium hydroxide (TBAH); amines such as ammonia, diethylamine, 2,2,6,6-tetramethyl piperidine (HTMP), tertiary amines (such as but not limited to dimethylethyl amine, diisopropylethylamine, trimethylamine, triethylamine, tributylamine, N-methylmorpholine, N-methylpyrrolidine, 1,8-diazabicyclo[5.4.0]-7-undecene (DBU), 1,5-diazabicyclo[4.3.0]-5-nonene (DBN), or tetramethylenediamine (TMEDA)), aromatic amines (such as but not limited to pyridine, collidine, lutidine, picoline, quinoline, or N,N-dimethylaniline); alkali metal amides such as but not limited to lithium amide, lithium dimethylamide, lithium diisopropylamide (LDA), lithium tetramethylpiperidide (LiTMP), or alkali metal hexamethyldisilazanes (such as but not limited to potassium hexamethyldisilazane, (KHMDS), sodium hexamethyldisilazane (NaHMDS), or lithium hexamethyldisilazane (LiHMDS)); alkyl lithiums, alkenyl lithiums, alkynyl lithiums, or alk(en)(yn)yl lithiums such as but not limited to n-butyl lithium sec-butyllithium, isopropyllithium; alkyl magnesium halides, alkenyl magnesium halides, alkynyl magnesium halides, or alk(en)(yn)yl magnesium halides such as but not limited to methyl magnesium bromide.

As used herein, solvent refers to any liquid that completely or partially dissolves a solid, liquid, or gaseous solute, resulting in a solution such as but not limited to hexane, benzene, toluene, diethyl ether, chloroform, ethyl acetate, dichloromethane, carbon tetrachloride, 1,4-dioxane, tetrahydrofuran, glyme, diglyme, acetone, acetonitrile, dimethylformamide, dimethyl sulfoxide, dimethylacetamide, or N-methyl-2-pyrrolidone.

As used herein, dehydrating agent refers to any compound that promotes the formation of carboxamides from carboxylic acids, such as but not limited to thionyl chloride, sulfuryl chloride, a carbodiimide, an anhydride or a mixed anhydride, a phenol (such as but not limited to nitrophenol, pentafluorophenol, or phenol), or a compound of Formula (A):

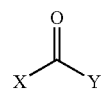

(A)

wherein each of X and Y is independently an unsubstituted or substituted heteroaryl group (such as but not limited to imidazolyl, benzimidazolyl, or benzotriazolyl). Examples of dehydrating agents further include, but are not limited to, benzotriazole-1-yl-oxy-tris-(dimethylamino)-phosphonium hexafluorophosphate (BOP), N,N'-carbonyldiimidazole (CDI), 3-(diethoxyphosphoryloxy)-1,2,3-benzotriazin-4 (3H)-one (DEPBT), 1-ethyl-3-(3-dimethyllaminopropyl)carbodiimide (EDC), 2-(7-aza-1H-benzotriazole-1-yl)-1,1,3,3-tetramethyluronium hexafluorophosphate (HATU), 2-(1H-benzotriazole-1-yl)-1,1,3,3-tetramethyluronium hexafluorophosphate (HBTU), 1-hydroxybenzotriazole (HOBt), benzotriazole-1-yl-oxy-tris-pyrrolidino-phosphonium hexafluorophosphate (PyBOP), 2-(1H-benzotriazole-1-yl)-1,1,3,3-tetramethyluronium tetrafluoroborate (TBTU), O-(3,4-dihydro-4-oxo-1,2,3-benzotriazine-3-yl)-N,N,N,N-tetramethyluronium tetrafluoroborate (TDBTU), 3-(diethyloxyphosphoryloxy)-1,2,3-benzotriazin-4(3H)-one (DEPBT), dicyclohexylcarbodiimide (DCC), N,N'-diisopropylcarbodiimide (DIC), or 1-hydroxy-7-azabenzotriazole (HOAt).

As used herein, acid refers to any compound that contains hydrogen and dissociates in water or solvent to produce positive hydrogen ions, as well as Lewis acids, including but not limited to hydrochloric acid, sulfuric acid, phosphoric acid, acetic acid, trihaloacetic acids (such as but not limited to trifluoroacetic acid or trichloroacetic acid), hydrogen bromide, maleic acid, sulfonic acids (such as but not limited to toluenesulfonic acids or camphorsulfonic acids), propionic acids (such as but not limited to (R)-chloropropionic acid), phthalamic acids (such as but not limited to N—[(R)-1-(1-naphthyl)ethyl]phthalamic acid), tartaric acids (such as but not limited to L-tartaric acid or dibenzyl-L-tartaric acid), lactic acids, camphoric acids, aspartic acids, or citronellic acids.

It is to be understood that reactants, compounds, solvents, acids, bases, catalysts, agents, reactive groups, or the like may be added individually, simultaneously, separately, and in any order. Furthermore, it is to be understood that reactants, compounds, acids, bases, catalysts, agents, reactive groups, or the like may be pre-dissolved in solution and added as a solution (including, but not limited to, aqueous solutions). In addition, it is to be understood that reactants, compounds, solvents, acids, bases, catalysts, agents, reactive groups, or the like may be in any molar ratio.

It is to be understood that reactants, compounds, solvents, acids, bases, catalysts, agents, reactive groups, or the like may be formed in situ.

5.2 Processes

Provided herein is a process for preparing a compound of Formula (I) or a pharmaceutically acceptable derivative thereof involving the step of reacting a compound of Formula (II) with the a compound of Formula (III) or a salt thereof as depicted in Scheme A below.

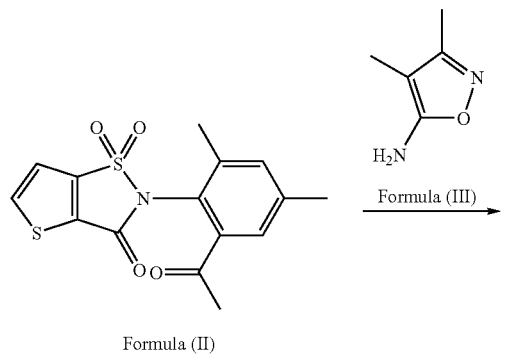

Formula (II)

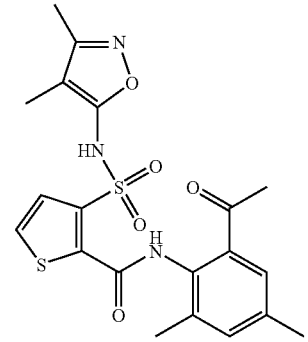

Formula (I)

The preparation of the compound of Formula (I) or a pharmaceutically acceptable derivative thereof as depicted in Scheme A may occur in the presence of any base or any combination of bases. In some embodiments, the base is (or combination of bases are) generated in situ. In some embodiments, the base is (or the combination of bases includes) an alkali metal hydride. In some embodiments, the base is sodium hydride.

The preparation of the compound of Formula (I) or a pharmaceutically acceptable derivative thereof as depicted in Scheme A may occur in any solvent or any combination of solvents. In some embodiments, the solvent is (or the combination of solvents contains) 1,4-dioxane, tetrahydrofuran, acetone, acetonitrile, dimethylformamide, dimethyl sulfoxide, glyme, diglyme, dimethylacetamide, or N-methyl-2-pyrrolidone. In some embodiments, the solvent is dimethylformamide.

In some embodiments of the preparation of the compound of Formula (I) or a pharmaceutically acceptable derivative thereof as depicted in Scheme A, the base is sodium hydride and the solvent is dimethylformamide.

The preparation of the compound of Formula (I) or a pharmaceutically acceptable derivative thereof as depicted in Scheme A may occur at any reaction temperature. In some embodiments, the reaction temperature may vary from about —78° C. to about 100° C. In some embodiments, the reaction temperature may vary from about −50° C. to about 80° C. In some embodiments, the reaction temperature may vary from about −40° C. to about 60° C. In some embodiments, the reaction temperature may vary from about −25° C. to about 30° C. In some embodiments, the reaction temperature may vary from about −10° C. to about 10° C. In some embodiments, the reaction temperature is about 0° C.

In some embodiments of the preparation of the compound of Formula (I) or a pharmaceutically acceptable derivative thereof as depicted in Scheme A, the base is sodium hydride, the solvent is dimethylformamide, and the reaction temperature is about 0° C.

The preparation of the compound of Formula (I) or a pharmaceutically acceptable derivative thereof as depicted in Scheme A may occur at any reaction time according to a person of ordinary skill in the art. In some embodiments, the reaction time is from about 30 minutes to about 24 hours. In some embodiments, the reaction time is from about 2 hours to about 3 hours.

In some embodiments of the preparation of the compound of Formula (I) or a pharmaceutically acceptable derivative thereof as depicted in Scheme A, the base is sodium hydride, the solvent is dimethylformamide, the reaction temperature is about 0° C., and the reaction time is from about 2 hours to about 3 hours.

The preparation of the compound of Formula (I) or a pharmaceutically acceptable derivative thereof as depicted in Scheme A may occur at any molar ratio according to a person of ordinary skill in the art. In some embodiments, the molar ratio of the compound of Formula (III) to the compound of Formula (II) is from about 3:1 to about 1:1. In other embodiments, the molar ratio of the compound of Formula (II) to the compound of Formula (III) is from about 3:1 to about 1:1. In some embodiments, the molar ratio of the compound of Formula (III) to the compound of Formula (II) is about 1:1.

In one embodiment of the preparation of the compound of Formula (I) or a pharmaceutically acceptable derivative thereof as depicted in Scheme A, the base is sodium hydride, the solvent is dimethylformamide, the reaction temperature is about 0° C., the reaction time is from about 2 hours to about 3 hours, and the molar ratio is about 1:1.

In another embodiment, provided is a process for preparing a compound of Formula (II) or a pharmaceutically acceptable derivative thereof by reacting a compound of Formula (IV) with a dehydrating agent or a combination of dehydrating agents as depicted in Scheme B.

Scheme B

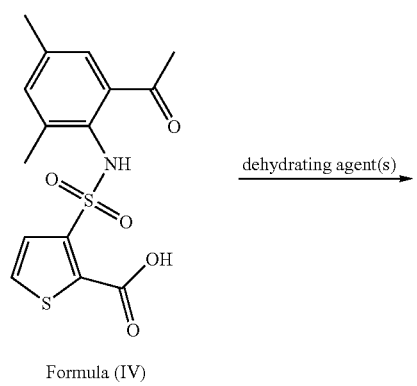

Formula (IV)

dehydrating agent(s)

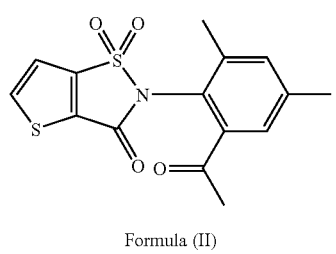

Formula (II)

In another embodiment, provided is a process for preparing a compound of Formula (II) or a pharmaceutically acceptable derivative thereof by reacting a compound of Formula (IVa) with a dehydrating agent of a combination of dehydrating agents as depicted in Scheme B1.

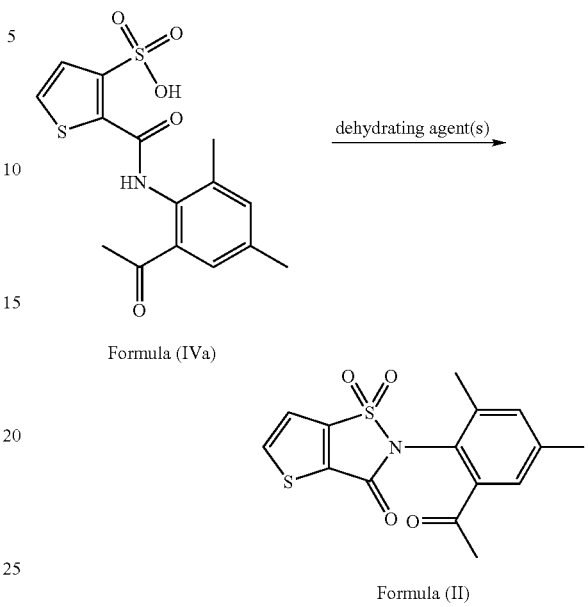

Scheme B1

Formula (IVa)

dehydrating agent(s)

Formula (II)

The preparation of the compound of Formula (IVa) may be prepared using methods known to those of ordinary skill in the art. For example, the compound of Formula (IVa) may be prepared using methods similar to those used in the preparation of the compound of Formula (IV).

The preparation of the compound of Formula (II) or a pharmaceutically acceptable derivative thereof as depicted in Scheme B or Scheme B1 may occur with any dehydrating agent or any combination of dehydrating agents according to a person of ordinary skill in the art. In some embodiments, the dehydrating agent is, or the combination of dehydrating agents are, generated in situ. In some embodiments, the dehydrating agent is (or the combination of dehydrating agents contains) thionyl chloride, sulfuryl chloride, 4-dimethylaminopyridine, a carbodiimide, an anhydride or a mixed anhydride, a phenol, or a compound of Formula (A):

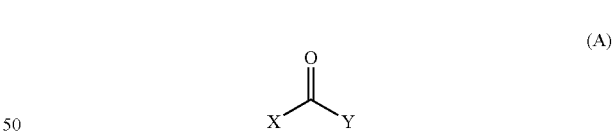

(A)

wherein each of X and Y is independently an unsubstituted or substituted heteroaryl group. In some embodiments, the dehydrating agent is (or combination of dehydrating agents contains) benzotriazole-1-yl-oxy-tris-(dimethylamino)-phosphonium hexafluorophosphate (BOP), N,N'-carbonyldiimidazole (CDI), 3-(diethoxyphosphoryloxy)-1,2,3-benzotriazin-4(3H)-one (DEPBT), 1-ethyl-3-(3-dimethyllaminopropyl)carbodiimide (EDC), 2-(7-aza-1H-benzotriazole-1-yl)-1,1,3,3-tetramethyluronium hexafluorophosphate (HATU), 2-(1H-benzotriazole-1-yl)-1,1,3,3-tetramethyluronium hexafluorophosphate (HBTU), 1-hydroxybenzotriazole (HOBt), benzotriazole-1-yl-oxy-tris-pyrrolidino-phosphonium hexafluorophosphate (PyBOP), 2-(1H-benzotriazole-1-yl)-1,1,3,3-tetramethyluronium tetrafluoroborate (TBTU), O-(3,4-dihydro-4-oxo-1,2, 3-benzotriazine-3-yl)-N,N,N-tetramethyluronium tetrafluoroborate (TDBTU), 3-(diethyloxyphosphoryloxy)-1,2,3-benzotriazin-4(3H)-one (DEPBT), dicyclohexylcarbodiimide (DCC), N,N'-diisopropylcarbodiimide (DIC), or 1-hydroxy-7-azabenzotriazole (HOAt). In some embodiments, the dehydrating agent is N,N'-carbonyldiimidazole.

The preparation of the compound of Formula (II) or a pharmaceutically acceptable derivative thereof as depicted in Scheme B or Scheme B1 may occur in any solvent or any combination of solvents. In some embodiments, the solvent is, or the combination of solvents contains, hexane, benzene, toluene, diethyl ether, chloroform, ethyl acetate, dichloromethane, carbon tetrachloride, 1,4-dioxane, tetrahydrofuran, glyme, diglyme, acetone, acetonitrile, dimethylformamide, dimethyl sulfoxide, dimethylacetamide, or N-methyl-2-pyrrolidone. In some embodiments, the solvent is ethyl acetate.

In some embodiments of the preparation of the compound of Formula (II) or a pharmaceutically acceptable derivative thereof as depicted in Scheme B or Scheme B1, the dehydrating agent is N,N'-carbonyldiimidazole and the solvent is ethyl acetate.

The preparation of the compound of Formula (II) or a pharmaceutically acceptable derivative thereof as depicted in Scheme B or Scheme B1 may occur at any reaction temperature according to a person of ordinary skill in the art. In some embodiments, the reaction temperature is from about 0° C. to about 100° C. In some embodiment, the reaction temperature is from about 20° C. to about 80° C. In some embodiments, the reaction temperature is from about 40° to about 60° C. In some embodiments, the reaction temperature is from about 20° C. to about 30° C.

In some embodiments of the preparation of the compound of Formula (II) or a pharmaceutically acceptable derivative thereof as depicted in Scheme B or Scheme B1, the dehydrating agent is N,N'-carbonyldiimidazole, the solvent is ethyl acetate, and the reaction temperature is from about 20° C. to about 30° C.

The preparation of the compound of Formula (II) or a pharmaceutically acceptable derivative thereof as depicted in Scheme B or Scheme B1 may occur at any reaction time according to a person of ordinary skill in the art. In some embodiments, the reaction time is from about 30 minutes to about 5 hours. In some embodiments, the reaction time is from about 3 hours to about 5 hours. In some embodiments, the reaction time is about 4 hours.

In some embodiments of the preparation of the compound of Formula (II) or a pharmaceutically acceptable derivative thereof as depicted in Scheme B or Scheme B1, the dehydrating agent is N,N'-carbonyldiimidazole, the solvent is ethyl acetate, the reaction temperature is from about 20° C. to about 30° C., and the reaction time is about 4 hours.

The preparation of the compound of Formula (II) or a pharmaceutically acceptable derivative thereof as depicted in Scheme B or Scheme B1 may occur at any molar ratio according to a person of ordinary skill in the art. In some embodiments, the molar ratio of N,N'-carbonyldiimidazole to the compound of Formula (IV) is from about 5:1 to about 1:1. In some embodiments, the molar ratio of N,N'-carbonyldiimidazole to the compound of Formula (IV) is about 1.2:1.

In one embodiment of the preparation of the compound of Formula (II) or a pharmaceutically acceptable derivative thereof as depicted in Scheme B or Scheme B1, the dehydrating agent is N,N'-carbonyldiimidazole, the solvent is ethyl acetate, the reaction temperature is from about 20° C. to about 30° C., the reaction time is about 4 hours, and the molar ratio of N,N'-carbonyldiimidazole to the compound of Formula (IV) is about 1.2:1.

In another embodiment, provided is a process for preparing a compound of Formula (IV) or a pharmaceutically acceptable derivative thereof from a compound of Formula (VI) as depicted in Scheme C.

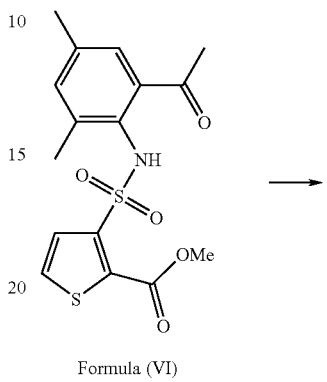

Formula (VI)

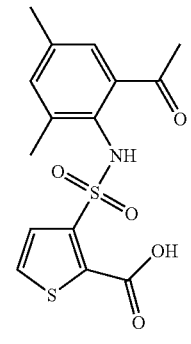

Formula (IV)

The preparation of the compound of Formula (IV) or a pharmaceutically acceptable derivative thereof as depicted in Scheme C may occur in the presence of any base or any combination of bases. In some embodiments, the base is (or the combination of bases are) generated in situ. In some embodiments, the base is (or the combination of bases contains) a hydroxide. In some embodiments, the base is (or the combination of bases contains) potassium hydroxide, sodium hydroxide, lithium hydroxide, magnesium hydroxide, calcium hydroxide, or barium hydroxide. In some embodiments, the base is sodium hydroxide.

The preparation of the compound of Formula (IV) or a pharmaceutically acceptable derivative thereof as depicted in Scheme C may occur in any solvent or any combination of solvents according to a person of ordinary skill in the art. In some embodiments, the solvent is (or the combination of solvents contains) hexane, benzene, toluene, diethyl ether, chloroform, ethyl acetate, dichloromethane, carbon tetrachloride, 1,4-dioxane, tetrahydrofuran, glyme, diglyme, acetone, acetonitrile, dimethylformamide, dimethyl sulfoxide, dimethylacetamide, or N-methyl-2-pyrrolidone. In some embodiments, the solvent is tetrahydrofuran.

In some embodiments of the preparation of the compound of Formula (IV) or a pharmaceutically acceptable derivative thereof as depicted in Scheme C, the base is sodium hydroxide and the solvent is tetrahydrofuran.

The preparation of the compound of Formula (IV) or a pharmaceutically acceptable derivative thereof as depicted in Scheme C may occur at any reaction temperature according to a person of ordinary skill in the art. In some embodiments, the reaction temperature is from about 0° C. to about 100° C. In some embodiments, the reaction temperature is from about 20° C. to about 80° C. In some embodiments, the reaction temperature is from about 40° to about 60° C. In some embodiments, the reaction temperature is from about 20° C. to about 30° C.

In some embodiments of the preparation of the compound of Formula (IV) or a pharmaceutically acceptable derivative thereof as depicted in Scheme C, the base is sodium hydroxide, the solvent is tetrahydrofuran, and the reaction temperature is from about 20° C. to about 30° C.

The preparation of the compound of Formula (IV) or a pharmaceutically acceptable derivative thereof as depicted in Scheme C may occur at any reaction time according to a person of ordinary skill in the art. In some embodiments, the reaction time is from about 2 hours to about 36 hours.

In one embodiment of the preparation of the compound of Formula (IV) or a pharmaceutically acceptable derivative thereof as depicted in Scheme C, the base is sodium hydroxide, the solvent is tetrahydrofuran, the reaction temperature is from about 20° C. to about 30° C., and the reaction time is from about 2 hours to about 36 hours.

The preparation of the compound of Formula (IV) or a pharmaceutically acceptable derivative thereof as depicted in Scheme C may occur in the presence of any acid or any combination of acids according to a person of ordinary skill in the art. In some embodiments, the acid is (or combination of acids are) generated in situ.

In another embodiment, provided is a process for preparing a compound of Formula (VI) or a pharmaceutically acceptable derivative by reacting a compound of Formula (VII) with a compound of Formula (VIII) or a salt thereof as depicted in Scheme D.

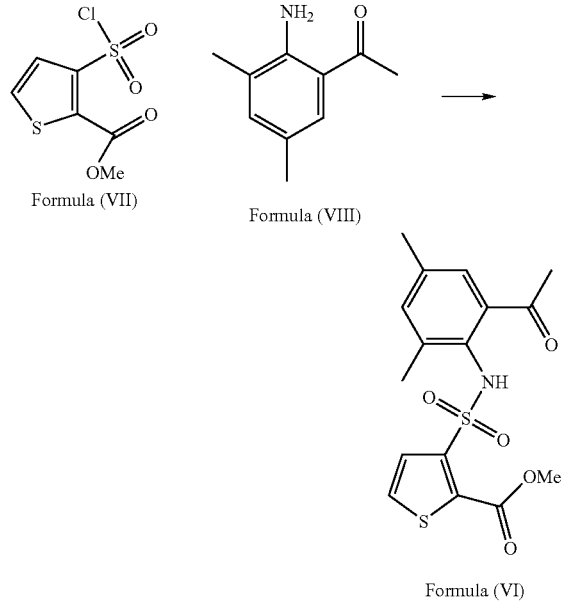

The preparation of the compound of Formula (VI) or a pharmaceutically acceptable derivative thereof as depicted in Scheme D may occur in the presence of any base or any combination of bases according to a person of ordinary skill in the art. In some embodiments, the base is (or combination of bases are) generated in situ. In some embodiments, the base is (or combination of bases contains) a tertiary amine, aromatic amine, non-nucleophilic alkali metal amide, alkyl lithium, alkenyl lithium, alkynyl lithium, alk(en)yn)(yl lithium, alkyl magnesium halide, alkenyl magnesium halide, alkynyl magnesium halide, or alk(en)(yn)yl magnesium halide. In some embodiments, the base is (or combination of bases contains) dimethylethyl amine, trimethylamine, triethylamine, tributylamine, N-ethyldiisopropylamine, N-methylmorpholine, 1,8-diazabicyclo[5.4.0]-7-undecene, 1,5-diazabicyclo[4.3.0]-5-nonene, tetramethylenediamine, pyridine, collidine, lutidine, picoline, quinoline, or N,N-dimethylaniline. In some embodiments, the base is pyridine.

The preparation of the compound of Formula (VI) or a pharmaceutically acceptable derivative thereof as depicted in Scheme D may occur at any reaction temperature according to a person of ordinary skill in the art. In some embodiments, the reaction temperature is from about 0° C. to about 100° C. In some embodiments, the reaction temperature is from about 20° C. to about 80° C. In some embodiments, the reaction temperature is from about 40° to about 60° C. In some embodiments, the reaction temperature is from about 20° C. to about 30° C.

In some embodiments of the preparation of the compound of Formula (VI) or a pharmaceutically acceptable derivative thereof as depicted in Scheme D, the base is pyridine and the reaction temperature is from about 20° C. to about 30° C.

The preparation of the compound of Formula (VI) or a pharmaceutically acceptable derivative thereof as depicted in Scheme D may occur at any reaction time according to a person of ordinary skill in the art. In some embodiments, the reaction time is from about 2 hours to about 36 hours.

In some embodiments of the preparation of the compound of Formula (VI) or a pharmaceutically acceptable derivative thereof as depicted in Scheme D, the base is pyridine, the reaction temperature is from about 20° C. to about 30° C., and the reaction time if from about 2 hours to about 36 hours.

The preparation of the compound of Formula (VI) or a pharmaceutically acceptable derivative thereof as depicted in Scheme D may occur in any solvent or any combination of solvents according to a person of ordinary skill in the art. Further, the preparation of the compound of Formula (VI) or a pharmaceutically acceptable derivative as depicted in Scheme D in the presence of a base or a combination of bases may occur in any solvent or combination of solvents according to a person of ordinary skill in the art. In some embodiments, the solvent is (or combination of solvents contains) hexane, benzene, toluene, diethyl ether, chloroform, ethyl acetate, dichloromethane, carbon tetrachloride, 1,4-dioxane, tetrahydrofuran, glyme, diglyme, acetone, acetonitrile, dimethylformamide, dimethyl sulfoxide, dimethylacetamide, and N-methyl-2-pyrrolidone.

The preparation of the compound of Formula (VI) or a pharmaceutically acceptable derivative thereof as depicted in Scheme D may occur at any molar ratio according to a person of ordinary skill in the art. In some embodiments, the molar ratio of the compound of Formula (VIII) to the compound of Formula (VII) is from about 3:1 to about 1:1. In other embodiments, the molar ratio of the compound of Formula (VII) to the compound of Formula (VIII) is from about 3:1 to about 1:1. In some embodiments, the molar ratio of the compound of Formula (VIII) to the compound of Formula (VII) is about 1.1:1.

In one embodiment of the preparation of the compound of Formula (VI) or a pharmaceutically acceptable derivative thereof as depicted in Scheme D, the base is pyridine, the reaction temperature is from about 20° C. to about 30° C., the reaction time if from about 2 hours to about 36 hours, and the molar ratio of the compound of Formula (VIII) to the compound of Formula (VII) is about 1.1:1.

The following examples are for illustration only and are not intended to limit the scope of this disclosure.

EXAMPLE 1

Preparation of N-(2-acetyl-4,6-dimethylphenyl)-3-{[(3,4 dimethyl-5-isoxazolyl)amino]sulfonyl}-2-thiophenecarboxamide At 0° C.: To 1.6 g 60% NaH in mineral oil was added a solution of 1.12 g of the compound of Formula (III) in 10 ml DMF. After stirring for 15 minutes a solution of 3.35 g of the compound of Formula (II) in 10 ml DMF was added drop wise. Alternatively, the compound of Formula (II) was added to the NaH first, followed by addition of the compound of Formula (III). As another alternative, the compounds of Formulae (II) and (III) were added simultaneously to the NaH. The reaction was stirred for 2 hours followed by a slow addition of 50 ml 2 N HCl (caution, excess NaH). The resulting suspension was extracted with toluene (4×25 ml). The organic layers were combined and washed with 2 N HCl (4×25 ml) followed by extraction with sat. NaHCO$_3$ (4×10 ml). The bicarbonate layers were combined and acidified with conc. HCl to pH ~1-2 and extracted with EtOAc (3×25 ml). The EtOAc layers were combined and washed with 2 N HCl (25 ml), 2 N HCl/brine (25 ml), dried over MgSO$_4$ and concentrated in vacuo to yield 4.0 g TBC3711 as a tan solid with a purity >97%. Crystallization of 3.2 g crude N-(2-acetyl-4,6-dimethylphenyl)-3-{[(3,4 dimethyl-5-isoxazolyl)amino]sulfonyl}-2-thiophenecarboxamide from hot EtOH gave 2.75 g of the title compound as an off white solid in >99% purity by HPLC. $^1$H NMR (500 MHz, DMSO-d$_6$): δ 1.65 (s, 3H), 2.08 (s, 3H), 2.22 (s, 3H), 2.32 (s, 3H), 2.47 (s, 3H), 7.27 (brs, 1H), 7.33 (d, J=5.2 Hz, 1H), 7.38 (brs, 1H), 7.86 (d, J=5.2 Hz, 1H) and 10.26 (brs, 1H). $^{13}$C NMR (125 MHz, DMSO-d$_6$): δ 5.8, 10.3, 17.7, 20.4, 29.1, 105.7, 126.5, 127.9, 128.7, 129.8, 133.9, 135.8, 136.2, 136.5, 138.3, 139.9, 155.2, 159.1, 161.4 and 200.5 ppm. MS (ESI) m/z: 446.08 [M−H]$^-$.

EXAMPLE 2

Preparation of the Compound of Formula (II)

To a solution of 5.7 g of the compound of Formula (IV) in 60 ml EtOAc was added 3.1 g CDI. After stirring for 4 hours the reaction mixture was concentrated in vacuo. Crystallization from hot EtOAc gave 4.25 g of the compound of Formula (II) as a white solid in >99% by HPLC. $^1$H NMR (400 MHz, CDCl$_3$): δ 2.40 (s, 3H), 2.43 (s, 3H), 2.53 (s, 3H), 7.35 (brs, 1H), 7.41 (d, J=5.1 Hz, 1H), 7.45 (brs, 1H) and 7.91 (d, J=5.1 Hz, 1H) ppm. MS (ESI) m/z: 693.08 [2M+H]$^+$, and 336.00 [M+H]$^+$.

EXAMPLE 3

Preparation of the Compound of Formula (IV)

To a solution of 6.25 g of the compound of Formula (VI) in 60 ml THF was added 30 ml 2N NaOH. After overnight stirring the reaction mixture was quenched with 10 ml conc. HCl followed by extraction with EtOAc (2×). The organic layers were combined and washed with 2 N HCl (2×), 2N HCl/brine (1×), dried over MgSO$_4$ and concentrated in vacuo to yield 6.0 g of the compound of Formula (IV) as a light green sticky foam. Tituration with DCM gave the product as a dry white solid in >99% purity by HPLC. $^1$H NMR (400 MHz, CDCl$_3$): δ 2.14 (s, 3H), 2.28 (s, 3H), 2.31 (s, 3H), 7.17 (d, J=5.1 Hz, 1H), 7.27 (brs, 1H), 7.30 (brs, 1H), 7.64 (d, J=5.1 Hz, 1H) and 8.91 (brs, 1H) ppm. MS (ESI) m/z: 720.08 [2M+H]$^+$, 376.04 [M+Na]$^+$ and 354.06 [M+H]$^+$.

EXAMPLE 4

Preparation of the Compound of Formula (VI)

To a solution of 4.4 g of the compound of Formula (VIII) in 20 ml pyridine was added 6.0 g the compound of Formula (VII). The reaction mixture was stirred overnight followed by addition of 50 ml 6 N HCl. The resulting suspension was extracted with DCM (2×). The organic layers were combined and washed with 2 N HCl (2×), 2 N HCl/brine, dried over MgSO$_4$ and concentrated in vacuo. Crystallization from hot EtOAc/hexanes (1:1, 20 ml) gave 6.33 g of the compound of Formula (VI) as an off-white solid in >99% purity by HPLC. $^1$H NMR (400 MHz, CDCl$_3$): δ 2.14 (s, 3H), 2.32 (s, 3H), 2.42 (s, 3H), 4.04 (s, 3H), 7.18 (brs, 1H), 7.22 (brs, 1H), 7.28 (d, J=5.1 Hz, 1H), 7.40 (d, J=5.1 Hz, 1H) and 9.16 (brs, 1H) ppm. MS (ESI) m/z: 757.12 [2M+H]$^+$ and 368.04 [M+H]$^+$.

Since modifications would be apparent to those of skill in the art, this disclosure is intended to be limited only by the appended claims.

What is claimed:

1. A process for preparing a compound of Formula (I):

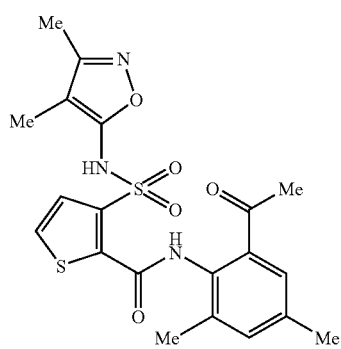

(I)

or a pharmaceutically acceptable derivative thereof, comprising a step of reacting a compound of Formula (II):

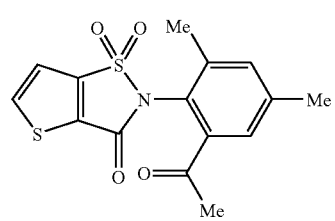

(II)

with a compound of Formula (III):

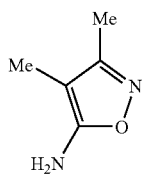

or a salt thereof.

2. The process of claim 1, wherein the reaction occurs in presence of a base or a combination of bases.

3. The process of claim 2, wherein the base is, or the combination of bases comprises, an alkali metal hydride.

4. The process of claim 3, wherein the base is, or the combination of bases comprises, sodium hydride, lithium hydride, or potassium hydride.

5. The process of claim 4, wherein the base is sodium hydride.

6. The process of claim 1, wherein the reaction occurs in a solvent or a combination of solvents.

7. The process of claim 6, wherein the solvent is, or the combination of solvents comprises, 1,4-dioxane, tetrahydrofuran, acetone, acetonitrile, dimethylformamide, dimethyl sulfoxide, glyme, diglyme, dimethylacetamide, or N-methyl-2-pyrrolidone.

8. The process of claim 7, wherein the solvent is dimethylformamide.

9. The process of claim 2, wherein the base is, or the combination of bases comprises, an alkyl lithium, an alkenyl lithium, an alkynyl lithium, an alk(en)(yn)yl lithium, an alkyl magnesium halide, an alkenyl magnesium halide, an alkynyl magnesium halide, an alk(en)(yn)yl magnesium halide, an alkali metal amide, tertiary amine, or aromatic amine.

10. The process of claim 9, wherein the reaction occurs in a solvent or a combination of solvents.

11. The process of claim 10, wherein the solvent is, or the combination of solvents comprises, 1,4-dioxane, tetrahydrofuran, dimethylformamide, dimethyl sulfoxide, glyme, diglyme, dimethylacetamide, or N-methyl-2-pyrrolidone.

12. The process of claim 1, wherein the reaction temperature is from about −78° C. to about 100° C.

13. The process of claims 1, wherein the reaction temperature is about 0° C.

14. The process of claim 1, wherein the reaction time is from about 30 minutes to about 24 hours.

15. The process of claim 1, wherein the reaction time is from about 2 hours to about 3 hours.

16. The process of claim 1, wherein the molar ratio of the compound of Formula (III) to the compound of Formula (II) is from about 3:1 to about 1:1.

17. The process of claim 1, wherein the molar ratio of the compound of Formula (II) to the compound of Formula (III) is from about 3:1 to about 1:1.

18. The process of claim 1, wherein the molar ratio of the compound of Formula (III) to the compound of Formula (II) is about 1:1.

19. The process of claim 1, further comprising preparing the compound of Formula (II) by reacting a compound of Formula (IV):

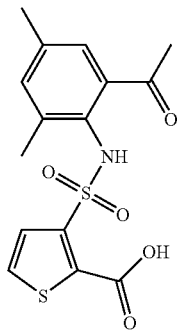

with a dehydrating agent or a combination of dehydrating agents.

20. A process of preparing a compound of Formula (II):

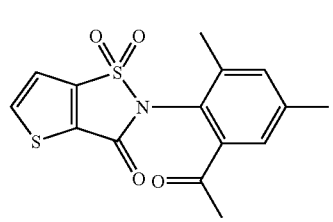

or a pharmaceutically acceptable derivative thereof, comprising the step of reacting a compound of Formula (IV):

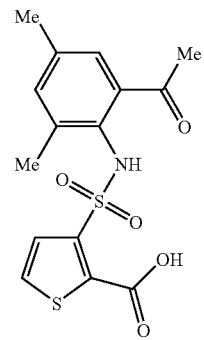

with a dehydrating agent or a combination of dehydrating agents.

21. The process of claims 19, wherein the dehydrating agent is, or the combination of dehydrating agents comprises, thionyl chloride, sulfuryl chloride, a carbodiimide, an anhydride or a mixed anhydride, a phenol, or a compound of Formula (A):

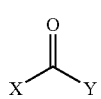

wherein each of X and Y is independently an unsubstituted or substituted heteroaryl group.

22. The process of claim 19, wherein the dehydrating agent is, or the combination of dehydrating agents comprises, benzotriazole-1-yl-oxy-tris-(dimethylamino)-phosphonium hexafluorophosphate, N,N'-carbonyldiimidazole, 3-(diethoxyphosphoryloxy)-1,2,3-benzotriazin-4(3H)-one, 1-ethyl-3-(3-dimethyllaminopropyl)carbodiimide, 2-(7-aza-1H-benzotriazole-1-yl)-1,1,3,3-tetramethyluronium hexafluorophosphate, 2-(1H-benzotriazole-1-yl)-1,1,3,3-tetramethyluronium hexafluorophosphate, 1-hydroxybenzotriazole, benzotriazole-1-yl-oxy-tris-pyrrolidino-phosphonium hexafluorophosphate, 2-(1H-benzotriazole-1-yl)-1,1,3,3-tetramethyluronium tetrafluoroborate, O-(3,4-dihyro-4-oxo-1,2,3-benzotriazine-3-yl-N,N,N,N-tetramethyluronium tetrafluoroborate, 3-(diethyloxyphosphoryloxy)-1,2,3-benzotriazin-4(3H-one, dicyclohexylcarbodiimide, N,N'-diisopropylcarbodiimide, or 1-hydroxy-7-azabenzotriazole, nitrophenol, pentafluorophenol, or phenol.

23. The process of claim 19, wherein the dehydrating agent is N,N'-carbodiimidazole.

24. The process of claim 19, wherein the reaction occurs in a solvent or a combination of solvents.

25. The process of claim 24, wherein the solvent is, or the combination of solvents comprises, hexane, benzene, toluene, diethyl ether, chloroform, ethyl acetate, dichloromethane, carbon tetrachloride, 1,4-dioxane, tetrahydrofuran, glyme, diglyme, acetone, acetonitrile, dimethylformamide, dimethyl sulfoxide, dimethylacetamide, or N-methyl-2-pyrrolidone.

26. The process of claim 24, wherein the solvent is ethyl acetate.

27. The process of claim 19, wherein the reaction temperature is from about 0° C. to about 100° C.

28. The process of claim 19, wherein the reaction temperature is from about 20° C. to about 30° C.

29. The process of claim 19, wherein the reaction time is from about 30 minutes to about 24 hours.

30. The process of claim 19, wherein the reaction time is from about 3 hours to about 5 hours.

31. The process of claim 19, wherein the reaction time is about 4 hours.

32. The process of claim 19, wherein the molar ratio of N,N'-carbonyldiimidazole to the compound of Formula (IV) is from about 5:1 to about 1:1.

33. The process of claim 19, wherein the molar ratio of N,N'-carbonyldiimidazole to the compound of Formula (IV) is about 1.2:1.

34. The process of claim 19, further comprising preparing the compound of Formula (IV) by reacting a compound of Formula (VI):

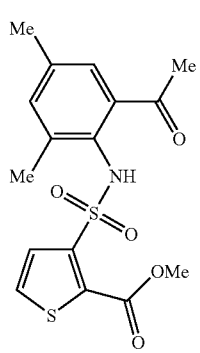

(VI)

with a base or a combination of bases.

35. The process of claim 34, further comprising preparing the compound of Formula (VI) by reacting a compound of Formula (VII):

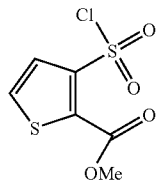

(VII)

with a compound of Formula (VIII):

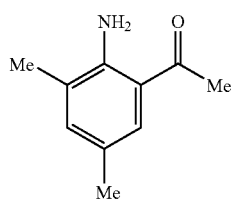

(VIII)

or a salt thereof.

36. The process of claim 35, wherein the reaction occurs in the presence of a base or a combination of bases.

37. The process of claim 36, wherein the base is, or the combination of bases comprises, a tertiary amine, aromatic amine, non-nucleophilic alkali metal amide, alkyl lithium, alkenyl lithium, alkynyl lithium, alk(en)(yn)yl lithium, alkyl magnesium halide, alkenyl magnesium halide, alkynyl magnesium halide, or alk(en)(yn)yl magnesium halide.

38. The process of claim 36, wherein the base is, or the combination of bases comprises, dimethylethyl amine, trimethylamine, triethylamine, tributylamine, N-ethyldiisopropylamine, N-methylmorpholine, 1,8-diazabicyclo[5.4.0]-7-undecene, 1,5-diazabicyclo[4.3.0]-5-nonene, tetramethylenediamine, pyridine, picoline, quinoline, or N,N-dimethylaniline.

39. The process of claim 36, wherein the base is pyridine.

40. The process of claim 35, wherein the reaction occurs in a solvent or a combination of solvents.

41. The process of claim 40, wherein the solvent is, or combination of solvents comprises, hexane, benzene, toluene, diethyl ether, chloroform, ethyl acetate, dichloromethane, carbon tetrachloride, 1,4-dioxane, tetrahydrofuran, glyme, diglyme, acetone, acetonitrile, dimethylformamide, dimethyl sulfoxide, dimethylacetamide, and N-methyl-2-pyrrolidone.

42. The process of claim 35, wherein the reaction temperature is from about 0° C. to about 100° C.

43. The process of claim 35, wherein the reaction temperature is from about 20° C. to about 30° C.

44. The process of claim 35, wherein the reaction time is from about 2 hours to about 36 hours.

45. The process of claim 35, wherein the reaction time is from about 8 hours to about 12 hours.

46. The process of claim 35, wherein the molar ratio of the compound of Formula (VIII) to the compound of Formula (VII) is from about 3:1 to about 1:1.

47. The process of claim 35, wherein the molar ratio of the compound of Formula (VIII) to the compound of Formula (VII) is about 1.1:1.

48. The process of claim 35, wherein the molar ratio of the compound of Formula (VII) to the compound of Formula (VIII) is from about 3:1 to about 1:1.

* * * * *